United States Patent [19]
Benson et al.

[11] Patent Number: 4,555,661
[45] Date of Patent: Nov. 26, 1985

[54] METHOD AND APPARATUS FOR DETERMINING DIELECTRIC CONSTANT

[75] Inventors: Warren E. Benson, Needham; Stanley Breen, Norwood, both of Mass.

[73] Assignee: Forte Technology, Inc., Norwood, Mass.

[21] Appl. No.: 483,857

[22] Filed: Apr. 11, 1983

[51] Int. Cl.⁴ .................. G01N 27/02; G01R 27/26
[52] U.S. Cl. .................. 324/61 R; 324/61 P; 324/61 QS
[58] Field of Search ............... 340/870.37; 324/61 R, 324/61 P, 61 QS, 65 P

[56] References Cited

U.S. PATENT DOCUMENTS

| 3,025,465 | 3/1962 | Breen | 324/61 R |
| 3,297,941 | 1/1967 | Wolfendale | 324/61 QS |
| 3,436,320 | 4/1969 | Marsh | 324/65 P |
| 3,488,758 | 1/1970 | Benson | 324/61 R |
| 4,219,776 | 8/1980 | Arulanandan | 324/61 P X |

FOREIGN PATENT DOCUMENTS 0642639 1/1979 U.S.S.R. .............. 324/61 P

Primary Examiner—Stanley T. Krawczewicz
Assistant Examiner—Jose M. Solis
Attorney, Agent, or Firm—Davis Hoxie Faithfull & Hapgood

[57] ABSTRACT

An improved method and apparatus for determining the dielectric constant of materials which flow using capacitive techniques, having an electrode device with at least two output terminals and three or more electrodes spaced at fixed distances from one another. At least two of the electrodes are connected through a switch so that first and second capacitances appear at the output terminals of the electrode device depending upon the position of the switch. The output terminals of the electrode device being connected to an oscillator which produces an output signal indicative of the frequency of the oscillator's oscillation which is proportional to the capacitance at the terminals of the electrode device. The output signal of the oscillator is connected to a bi-directional counter or microprocessor which is used to calculate a value proportional to the change in capacitance of the electrode device when the switch is closed and to thereby determine the dielectric constant of a material being tested.

30 Claims, 7 Drawing Figures

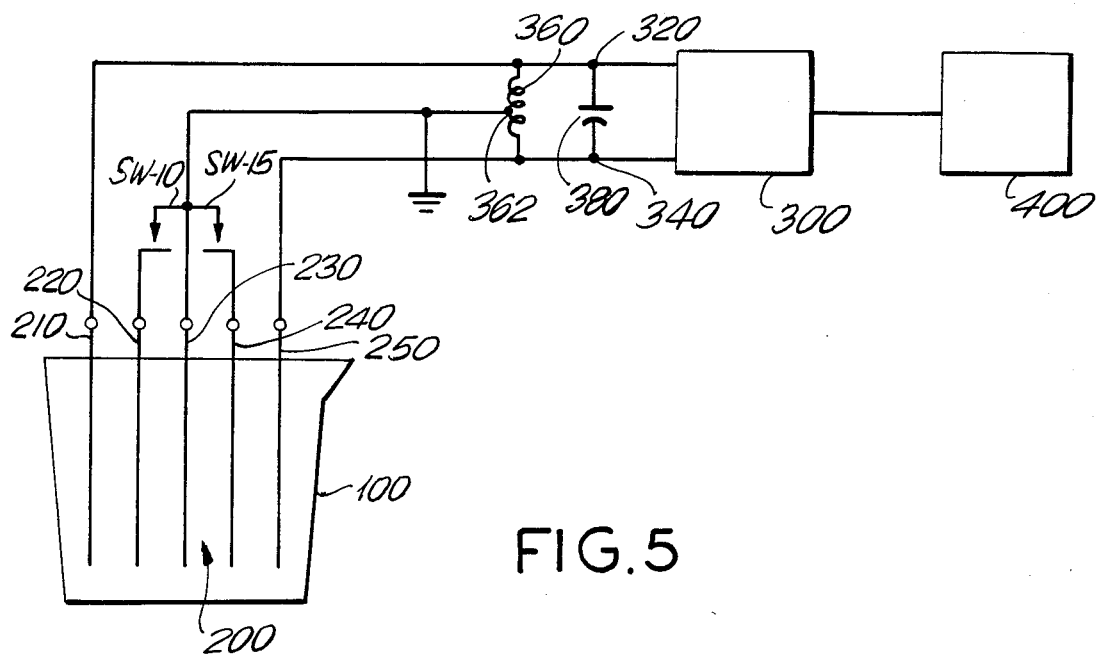
FIG.5
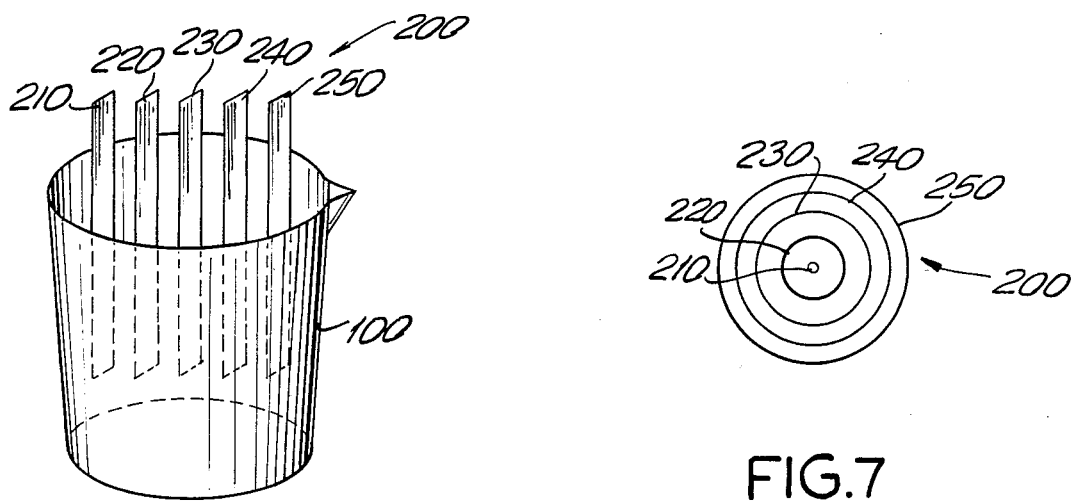
FIG.6
FIG.7

METHOD AND APPARATUS FOR DETERMINING DIELECTRIC CONSTANT

FIELD OF THE INVENTION

This invention relates to an improved method and apparatus for determining the dielectric constant of liquids, slurries, gases, or solids that can be made to flow.

BACKGROUND OF THE INVENTION

The dielectric constant of a material is a fundamental physical property of the material and is important in research and development and for the control of industrial processes. For example, careful control of the amount of water in the oil being processed is important in the formulation of margarine. Since the dielectric constants of water and oil are quite different (water 80, oil ~3) a technique to rapidly, conveniently and accurately measure the dielectric constant of a mixture of water and oil to be processed is very useful in formulating margarine. One way of determining dielectric constant involves capacitance measuring, as the capacitance of a capacitor is proportional to a constant determined by the physical dimensions of the electrodes of the capacitor and the distance between the electrodes multiplied by the dielectric constant of the material between the electrodes. For example the capacitance, C, in farads of a parallel plate capacitor is approximated by the well known equation $C = K(\epsilon A)/d$, where K is a constant, $\epsilon$ is the dielectric constant of the material between the plates of the capacitor, A is the area of the plates and d is the distance between the plates. In addition to the area of the electrodes and the distance between them, the "end effects" of the electrodes affect the capacitance.

One technique for determining dielectric constant by capacitance methods is shown in U.S. Pat. No. 3,025,465, assigned to the assignee of the present application. In that patent, a sample of material is placed in a test cell which consists of two plates separated by a certain fixed distance. A first set of capacitance measurements is taken, first with the test cell empty and then with the material in the cell. Then, the spacing between the plates is changed by physically moving one of the plates. A second set of capacitance measurements is taken, first with the cell empty and then with the material in the cell. The dielectric constant of the material is determined from the ratio of the difference between the capacitances measured with the material in the test cell and the difference between the capacitances measured with the test cell empty, that is, filled only with air which has a known dielectric constant.

The difference between the capacitances measured with the test cell empty can also be used to calibrate a measuring instrument. Then, the dielectric constant of an unknown material can be determined using the difference between the capacitances measured with the unknown material in the test cell in conjunction with the calibrated measuring instrument. Further details of such measuring techniques are found in U.S. Pat. No. 3,025,465.

U.S. Pat. No. 3,488,758, assigned to the assignee of the present application, also utilizes a capacitance measuring method for determining dielectric constant. However, in that patent, capacitance is not measured directly. Rather, the plates of the test cell are connected across the terminals of a free running oscillator. The capacitance across the plates of the cell serves as the capacitance of the oscillator. The frequency of the oscillator is gated to a counter so as to produce an increasing count for a predetermined time interval during which the plates are separated by a first distance, followed by a decreasing count for a predetermined interval during which the plates are separated by a second distance. As in U.S. Pat. No. 3,025,465, the distance between the plates of the test cell is changed by moving one of the plates after the first measurement. The residual count remaining on the counter is a count proportional to the change in capacitance as a result of movement of the plates. As described above, the dielectric constant of the material can then be determined using a second set of differential measurements for a material having a known dielectric constant, for example, air.

Both of the above patents require that a plate be moved in carrying out the measurement process. Movement of a plate adds time, complexity and cost to the measurement process and also increases the probability of measurement error because position measurement of the movable plate is not perfectly repeatable.

SUMMARY OF THE INVENTION

The present invention relates to an improved method and apparatus for determining the dielectric constant of liquids, slurries, gases or solids that can be made to flow. According to the present invention, a differential capacitance technique is used. It is a feature of this invention that both the area and the end effects of the electrodes are held essentially constant. Consequently, the measured change in capacitance is due primarily to the change in distance between the electrodes.

The apparatus consists of a three electrode device which is placed in a vial containing a material for which the dielectric constant is to be determined. The electrode device is commonly known in the art as a "test cell". The electrodes may be arranged in a coaxial or planar relation and are physically spaced fixed distances from one another.

Two of the electrodes are connected across the terminals of a free-running oscillator. The third electrode is located between the first and second electrodes. A switch is connected between the first electrode and the third electrode so that the third electrode is at a floating potential when the switch is open. Closing the switch, electrically switches the third electrode from a floating potential to an electrical potential equal to that of the first electrode. In one embodiment, the switch is a reed relay which provides fast and reliable switching while introducing little stray capacitance and insuring a uniform low contact capacitance.

The first and second electrodes are connected to a free-running oscillator which is in turn connected to a counter. With the switch open, the capacitance for the free-running oscillator is primarily determined by the area of the first and second electrodes, the separation of the electrodes and the dielectric constant of the material between those electrodes. A first count of the frequency of the oscillator is provided by the counter which in one embodiment is a bi-directional counter. This first count from the bi-directional counter is an increasing count made during a predetermined time, for example, one second.

The switch is then closed, thereby electrically switching the third electrode to the electrical potential of the first electrode, and thus changing the value of the capacitance of the free-running oscillator because the distance between the two "plates" of the capacitor has effectively been decreased. A second count of the frequency of the oscillator is made by the counter. For the bi-directional counter, this count is in a decreasing direction for the same predetermined time period as used for the first count, leaving a residual count in the bi-directional counter.

The dielectric constant of a first material is determined as follows. A residual count is obtained using the above procedure for a second material having a known dielectric constant. Then, a residual count for the first material is obtained. Since the ratio of the unknown dielectric constant of the first material to the known dielectric constant of the second material is proportional to the ratio of the residual counts for the two materials, the dielectric constant of the unknown material can be readily determined from the measured residual counts.

In a further embodiment, a microprocessor is employed. The microprocessor replaces the counter and performs the counting function, controls the switch, and determines the dielectric constant, for example, by interpolating from a stored table of residual counts for materials of known dielectric constants. In another embodiment of the invention, five electrodes are used in a split stator arrangement, with two switches. This arrangement is particularly advantageous where a balanced electric field is desired.

BRIEF DESCRIPTION OF THE DRAWINGS

FIG. 5 is a block diagram of a second embodiment of the present invention utilizing a split stator electrode device.

FIG. 6 is an elevational view of one suitable arrangement for the electrodes of the split stator electrode device of FIG. 5, and FIG. 7 is a top view of a second suitable arrangement (coaxial) for the electrodes of the split stator electrode device of FIG. 5.

DETAILED DESCRIPTION OF THE EMBODIMENTS

Figure 1:
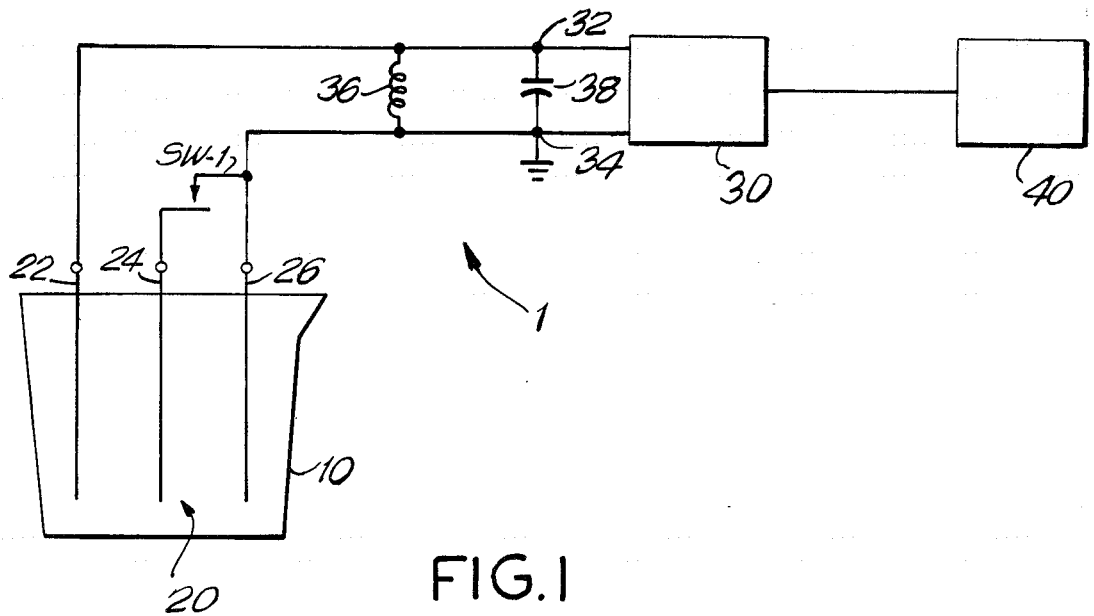
FIG. 1 is a block diagram of a first embodiment of the present invention including an electrode device.
Figure 2:
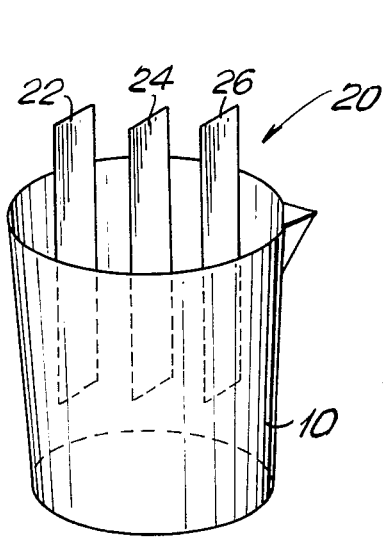
FIG. 2 is an elevational view of one suitable arrangement of the electrodes of the electrode device of FIG. 1.
Figure 3:
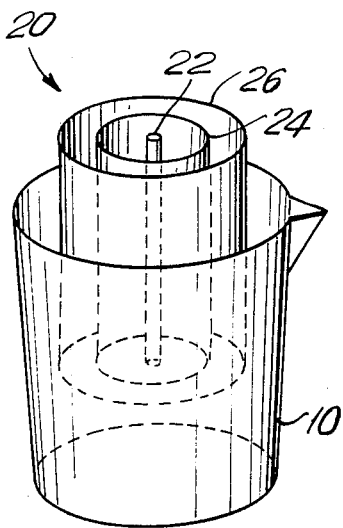
FIG. 3 is an elevational view of a second suitable arrangement (coaxial) of the electrodes of the electrode device of FIG. 1.
Figure 4:
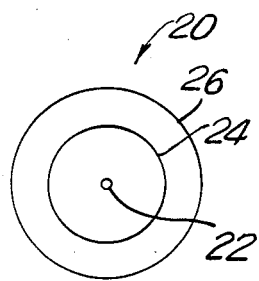
FIG. 4 is a top view of the electrodes of the electrode device of FIG. 3.

FIG. 1 shows a block diagram of a system 1 according to a first embodiment for determining the dielectric constant of a material in accordance with the present invention. System 1 includes an electrode device 20 having electrodes 22, 24 and 26. Electrode device 20 is shown schematically in FIG. 1 and the electrodes 22, 24 and 26, which are spaced fixed distances from one another, may suitably be arranged in a planar or a coaxial arrangement as illustrated by FIGS. 2 and 3 respectively.

Electrode 22 is connected to a first terminal 32 of a free-running oscillator 30. Electrode 26 is connected to a switch SW-1 and to a second terminal 34 of the free-running oscillator 30. A capacitor 38 and an inductor 36 are connected across the terminals 32 and 34 of the oscillator 30. The terminal 34 in this embodiment is also connected to ground. Electrode 24 is connected through the switch SW-1 to the electrode 26 so that when SW-1 is open electrode 24 is at a floating potential and when SW-1 is closed electrode 24 is connected to electrode 26 and terminal 34. The oscillator 30 produces a buffered output signal indicative of the frequency of oscillation of oscillator 30. The form of this buffered output signal is such that the pulsations of the output signal can be counted by a counter. This output signal is connected to an input of a counter 40, which in one embodiment is a bi-directional counter.

System 1 functions to determine the dielectric constant of a material as follows. The electrode device 20 is placed into a vial 10 which contains the material for which the dielectric constant is to be determined or in other words, the test material. This test material may suitably be any material that can be poured, for example, a liquid, slurry, gas, or a solid that can be made to completely fill the interelectrode spaces.

Initially, the electrodes 22 and 26 are connected across the terminals 32 and 34 of the free-running oscillator 30. Switch SW-1 is open, and thus electrode 24 initially is at a free floating electrical potential. The area of the electrodes 22 and 26, the distance between electrodes 22 and 26 and the dielectric constant of the material in vial 10 determine the capacitance as measured across the electrodes 22 and 26. The frequency of the oscillator 30 will vary in proportion to the capacitance contributed by the electrode device 20.

With the test material filling the interelectrode space and switch SW-1 open, the bi-directional counter 40 counts the number of pulses in the output signal of oscillator 30 occurring in a predetermined time, for example, one second. The counter 40 makes this first count in an increasing direction. In other words, during the first count, counter 40 counts "up".

A second count is made in the following manner. The switch SW-1 is closed, thus electrically switching electrode 24 to an electrical potential equal to that of electrode 26. With the switch SW-1 closed, the capacitance of electrode device 20 is determined by the area of electrodes 22 and 24, the distance between them, and the dielectric constant of the test material. For the planar electrode arrangement of FIG. 2, the areas of electrodes 22, 24 and 26 are equal and only the distance between the operative electrodes, electrode 22 and either electrode 24 or electrode 26 depending on whether SW-1 is closed or opened, changes when switch SW-1 is closed. This change in distance changes the value of the capacitance seen at the terminals of the electrode device 20.

The changed value of capacitance changes the frequency of oscillator 30. While switch SW-1 is closed, the bi-directional counter 40 counts the output pulses from the oscillator 30 in a decreasing direction for the same time period as used during the first count. In other words, counter 40 counts "down". Following the second count, a residual count is left in the counter 40. This residual count represents the change in frequency from the first to the second measurement. This change in frequency is a result of the change in capacitance seen at the terminals of the electrode device 20 between the first and second measurements. Consequently, the residual value of the counter 40 can be used to determine the dielectric constant of the test material in the vial 10 in an analogous manner to that which is explained in U.S. Pat. Nos. 3,025,465 and 3,488,758, which are herein incorporated by reference.

By way of example, the dielectric constant of the test material can be determined from the residual count by conducting similar differential measurements using a material with a known dielectric constant, for example, air which has a dielectric constant of 1. In U.S. Pat. No. 3,025,465, the dielectric constant of an unknown test material is found in the ratio of the difference in capacitance measured with the unknown test material to the difference in capacitance measured with a known material. Alternatively, the dielectric constant of the unknown test material can be determined using a calibration chart produced using representative residual counts for materials of known dielectric constants.

In a preferred embodiment, the counter 40 is part of a microprocessor. The microprocessor is also used to provide a control signal to open switch SW-1 for a predetermined time period and count the pulses from oscillator 30. The microprocessor then directs that switch SW-1 be closed and a second count be made for the predetermined time period. The microprocessor subtracts the second count from the first count to obtain the frequency difference count. The dielectric constant of the unknown material is calculated directly by the microprocessor, for example, by interpolation from a conversion table prepared using known materials. This conversion table is stored in the memory of the microprocessor. Table 1 below is an example of such a table. The frequency difference of Table 1 is not directly proportional to dielectric constant because of factors such as the variance with respect to frequency of the "end effect" of the electrodes and the nonlinearity of frequency with respect to capacitance. Use of Table 1 reduces calculation errors such as the error due to "end effects".

TABLE 1

| MATERIALS | DIELECTRIC CONSTANT (HAND BOOK VALUES) (NATIONAL BUREAU OF STANDARDS CIR. 514) | FREQUENCY DIFFERENCE C.P.S. in cycles per second* |
|---|---|---|
| AIR | 1.00 | 1735 |
| MINERAL OIL | 2.15 | 2855 |
| CHLOROBENZENE | 5.71 | 6257 |
| 1,2 DICHLOROETHANE | 10.36 | 10,323 |
| ACETONE | 20.7 | 17,141 |
| METHANOL | 32.6 | 23,806 |
| ETHYLENE GLYCOL | 37 | 31,835 |

(*The frequency of the oscillator 30 with air dielectric for this test was 3.162 Megahertz.)

In a further preferred embodiment, the switch SW-1 is a commercially available reed relay. A reed relay provides fast, positive switching and has only a small stray capacitance. The usual configuration of a reed relay consists of a metal reed with a movable contact at one end and a fixed contact at the other end. The relay is mounted and sealed in a small glass tube. The relay is made of ferromagnetic material so that it may be activated (deflected) by a solenoid mounted externally to the glass reed. A small current through the solenoid may be generated by a manual switch or by some external electrical switching command, such as a command from a microprocessor.

FIG. 5 shows a second embodiment of the present invention. System 1000 includes an electrode device 200 having electrodes 210, 220, 230, 240 and 250. Electrode device 200 is shown schematically in FIG. 5 and the electrodes 210, 220, 230, 240 and 250, which are spaced fixed distances from one another, may suitably be arranged in a planar or a coaxial arrangement. FIG. 6 shows the electrode device 200 in a planar arrangement. FIG. 7 shows a top view of the electrode device 200 in a coaxial arrangement. This five electrode arrangement (planar or coaxial) is an alternative to the single-ended capacitor of the FIG. 1 embodiment and is called a split stator capacitor. The split stator arrangement provides balanced fields relative to ground, which is useful for some oscillator circuits. Also, the split stator arrangement is preferable to the single-ended capacitor at very high frequencies. Electrode 210 is connected to a first terminal 320 of a free-running oscillator 300. Electrode 250 is connected to a second terminal 340 of the oscillator 300. Capacitor 380 and inductor 360 are connected in parallel across terminals 320 and 340 of the oscillator 300. Inductor 360 has a center tap 362 which is grounded.

Electrode 230 is connected to the center tap 362 of inductor 360, and thus is at a ground potential. Electrode 230 is also connected to switches SW-10 and SW-15. Electrode 220 is connected through the switch SW-10 to the electrode 230 so that when SW-10 is open electrode 220 is at a floating potential and when SW-10 is closed electrode 220 is connected to electrode 230 and center tap 362, and thus is at ground potential. Electrode 240 is similarly connected through switch SW-15 to the electrode 230 such that electrode 240 is at a floating potential when switch SW-15 is open and is at ground potential when switch SW-15 is closed.

The oscillator 300 produces, as in the FIG. 1 apparatus, a buffered output signal indicative of the frequency of oscillation of oscillator 300. The form of this buffered output signal is such that the pulsations of the output signal can be counted by a counter. This output signal is connected to an input of a counter 400 which in one embodiment is a bi-directional counter.

System 1000 functions in a similar fashion as system 1 to determine dielectric constant. With an unknown test material filling the electrode space and switches SW-10 and SW-15 open, the bi-directional counter 400 counts the number of pulses in the output signal of oscillator 300 occurring in a predetermined time, for example, one second. The counter 400 makes this first count in an increasing direction. In other words, during the first count, counter 400 counts "up".

A second count is then made with switches SW-10 and SW-15 closed. As a result, electrodes 220 and 240 are at an electrical potential equal to that of electrode 230, during the second count. When the switches SW-10 and SW-15 are closed, the capacitance seen at the terminals of the electrode device 200 changes. This capacitance change results in a change in the frequency of oscillator 300. The bi-directional counter 400 counts a second count in a decreasing direction for the same time period as used for the first count. As described above with reference to the system 1 apparatus, the residual value in the counter 400 is proportional to the change in capacitance of the electrode device 200 between the first and second measurements. As discussed above, the dielectric constant of the material can be determined using this residual value. As in the FIG. 1 embodiment, the switches SW-10 and SW-15 can be reed relays.

In another embodiment, the counter 400 is part of a microprocessor. The microprocessor provides control signals to open the switches SW-10 and SW-15 for a predetermined time period and count the pulses from oscillator 300. The microprocessor then directs that switches SW-10 and SW-15 be closed and a second count be made for the predetermined time period. As described above with reference to system 1, the microprocessor subtracts the second count from the first count to obtain a frequency difference count. The microprocessor calculates the dielectric constant using this frequency difference count.

All further measurements and computations for the FIG. 5 apparatus are conducted in the same manner as described above for the FIG. 1 apparatus.

As one example of the flexibility of the embodiments of the invention which incorporate a microprocessor, a calibration mode can be included for these embodiments. In the calibration mode, the electrodes are placed in a reagent grade material, a storage location is selected for that material, a button is pressed so that a calibration test generating a frequency difference is made, and the frequency difference is stored with the standard dielectric constant for the material. For example, the materials of Table 1 might be assigned storage locations 1–7. To calibrate for acetone, the calibration mode is entered and the electrodes are immersed in reagent grade acetone. Then, acetone's storage location (5) is selected. At storage location 5, the National Bureau of Standards value of the dielectric constant, 20.7, has already been stored prior to calibration. Then, a calibration test button is pressed and a frequency difference is established and stored along with the value 20.7. This frequency difference will be approximately 17,141 cycles per second for an apparatus like that used to generate Table 1 but will vary slightly depending on variations from apparatus to apparatus. The calibration mode compensates for the fact that no two sets of electrodes will be exactly alike and for similar variations in dielectric testing apparatus.

We claim:

1. A method for measuring the dielectric constant of a material in a container comprising the steps of:
    placing an electrode device in the container said electrode device having first, second and third electrodes which are physically spaced relative to one another, with the third electrode located between the first and second electrodes;
    connecting the first and second of the electrodes across first and second terminals at first and second electrical potentials, respectively, and leaving the third electrode at a floating electrical potential;
    measuring across the first and second electrodes a first value of an electrical signal proportional to the product of the dielectric constant of the material and the distance between the first and second electrodes, while maintaining the area and the end effects of the electrodes essentially constant;
    electrically switching the third electrode from the floating electrical potential to an electrical potential equal to the first electrical potential;
    measuring across the second and third electrodes a second value of an electrical signal proportional to the product of the dielectric constant of the material and the distance between the second and third electrodes, while maintaining the area and the end effects of the electrodes essentially constant;
    computing a third value equal to the difference between the first and second values; and
    calculating the dielectric constant of the material based on the third value.

2. The method as in claim 1 wherein the first, second and third electrodes are in coaxial relation.

3. The method as in claim 1 wherein the first, second and third electrodes are in planar relation.

4. The method as in claim 1 wherein a reed relay is located between the first and third electrodes such that closing the relay electrically switches the third electrode from the floating electrical potential to an electrical potential equal to the first electrical potential.

5. The method as in claim 4 wherein a microprocessor closes the relay.

6. The method as in claim 1 wherein the first, second and third electrodes are physically spaced fixed distances from one another.

7. The method as in claim 1 wherein the first and second terminals are terminals of a free-running oscillator, and the first value is a first frequency of the oscillator with the first and second electrodes connected to the first and second terminals, respectively, and the third electrode at the floating potential, and the second value is a second frequency of the oscillator with the first and third electrodes connected to the first and second terminals, respectively.

8. The method as in claim 7 wherein a microprocessor measures the first value and the second value, computes the third value, and calculates the dielectric constant of the material based on the third value.

9. The method as in claim 7 including the step of gating a bi-directional counter to the oscillator wherein the counter counts in an increasing direction pulses at the first frequency for a predetermined time, counts in a decreasing direction pulses at the second frequency for a time period equal to the predetermined time, and produces a residual count equal to the third value.

10. A method for measuring the dielectric constant of a material in a container comprising the steps of:
    placing an electrode device in the container said electrode device having first, second, third, fourth and fifth electrodes which are physically spaced relative to one another, with the fifth electrode located between the second and third electrodes, the third electrode located between the fifth and the fourth electrodes, and the fourth electrode located between the first and third electrodes;
    connecting the first electrode to a first terminal at a first electrical potential, the second electrode to a second terminal at a second electrical potential, and the third electrode to a third terminal at a ground electrical potential, wherein the first electrical potential is across the first and third terminals and the second electrical potential is across the second and third terminals, respectively, and leaving the fourth and fifth electrodes at a floating electrical potential;
    measuring across the first and second electrodes a first value of an electrical signal proportional to the product of the dielectric constant of the material and the distance between the first and second electrodes, while maintaining the area and the end effects of the electrodes essentially constant;
    switching electrically the fourth and fifth electrodes to an electrical potential equal to the third electrical potential;
    measuring across the first and second electrodes a second value of an electrical signal proportional to the product of the dielectric constant of the material and the distance between the first and second electrodes, while maintaining the area and the end effects of the electrodes essentially constant; computing a third value equal to the difference between the first and second values; and calculating the dielectric constant of the material based on the third value.

11. The method as in claim 10 wherein the first, second, third, fourth and fifth electrodes are in coaxial relation.

12. The method as in claim 10 wherein the first, second, third, fourth and fifth electrodes are in planar relation.

13. The method as in claim 10 wherein a first reed relay is located between the third and fourth electrodes such that closing the first relay electrically switches the fourth electrode from the floating electrical potential to the ground electrical potential, and a second relay is located between the third and fifth electrodes such that closing the second relay electrically switches the fifth electrode from the floating electrical potential to the ground electrical potential.

14. The method as in claim 10 including the step of connecting the first and second terminals across a free running oscillator prior to measuring the first value, wherein the first value is a first frequency of the oscillator with the first and second electrodes connected to the first and second terminals, respectively, the third electrode at the ground electrical potential, and the fourth and fifth electrodes at the floating electrical potential, and the second value is a second frequency of the oscillator with the fourth and fifth electrodes connected to the ground electrical potential.

15. The method as in claim 10 wherein the first, second, third, fourth and fifth electrodes are physically spaced fixed distances from one another.

16. The method as in claim 13 wherein a microprocessor closes the first and second relays.

17. The method as in claim 14 including the step of gating a bi-directional counter to the oscillator wherein the counter counts in an increasing direction pulses at the first frequency for a predetermined time, counts in a decreasing direction pulses at the second frequency for a time period equal to the predetermined time, and produces a residual count equal to the third value.

18. Apparatus for measuring the dielectric constant of a material in a container comprising;
an electrode device with first, second, third, fourth and fifth electrodes physically spaced relative to one another, with the third electrode located between the fourth and fifth electrodes, the fourth electrode located between the first and third electrodes, and the fifth electrode located between the third and second electrodes;
first and second terminals at first and second electrical potentials, respectively;
a third terminal at a ground electrical potential;
means for connecting the first electrode to the first terminal, the second electrode to the second terminal, and the third electrode to the third terminal;
means for placing the fourth and fifth electrodes at a floating electrical potential;
means for switching electrically the fourth and fifth electrodes from the floating electrical potential to the ground electrical potential;
a measuring instrument for measuring across the first and second electrodes, with the third electrode at the ground electrical potential and the fourth and fifth electrode at the floating electrical potential, a first value of an electrical signal proportional to the product of the dielectric constant of the material and the distance between the first and second electrodes, wherein the area and the end effects of the electrodes are kept essentially constant, and for measuring across the first and second electrodes, with the fourth and fifth electrodes switched electrically to the ground electrical potential, a second value of an electrical signal proportional to the product of the dielectric constant of the material and the distance between the first and second electrodes, wherein the area and the end effects of the electrodes are kept essentially constant.

19. The method as in claim 8 further comprising the step of using the microprocessor to store a value for a standard dielectric constant.

20. The method as in claim 19 wherein a plurality of values for a plurality of standard dielectric constants of varying magnitudes are stored.

21. The method as in claim 20 wherein the dielectric constant of the material is calculated by interpolation from a stored value of magnitude comparable to the third value.

22. Apparatus for measuring the dielectric constant of a material in a container comprising:
an electrode device with first, second and third electrodes physically spaced relative to one another, with the third electrode located between the first and second electrodes;
first and second terminals at first and second electrical potentials, respectively;
means for connecting the first electrode to the first terminal and the second electrode to the second terminal;
means for placing the third electrode at a floating electrical potential;
means for electrically switching the third electrode from the floating electrical potential to an electrical potential equal to the first electrical potential;
a measuring instrument for measuring across the first and second electrodes, with the third electrode at the floating potential, a first value of an electrical signal proportional to the product of the dielectric constant of the material and the distance between the first and second electrodes, wherein the area and the end effects of the electrodes are kept essentially constant, and for measuring across the second and third electrodes, with the third electrode switched electrically to an electrical potential equal to the first electrical potential, a second value of an electrical signal proportional to the product of the dielectric constant of the material and the distance between the third and second electrodes, wherein the area and the end effects of the electrodes are kept essentially constant;
means for computing a third value equal to the difference between the first and second values; and
means for calculating the dielectric constant of the material based on the third value.

23. Apparatus as in claim 22 wherein the first, second and third electrodes are in coaxial relation.

24. Apparatus as in claim 22 wherein the first, second and third electrodes are in planar relation.

25. Apparatus as in claim 22 wherein the means for switching is a reed relay located between the first and third electrodes.

26. Apparatus as in claim 25 wherein a microprocessor closes the relay.

27. Apparatus as in claim 22 wherein the first, second and third electrodes are physically spaced fixed distances apart from one another.

28. Apparatus as in claim 22 including a freerunning oscillator connected across the first and second terminals wherein the first value is a first frequency of the oscillator with the first and second electrodes connected to the first and second terminals, respectively, and the third electrode at the floating electrical potential, and the second value is a second frequency of the oscillator with the third and second electrodes connected to the first and second terminals, respectively.

29. Apparatus as in claim 22 wherein the measuring instrument, the computing means and the calculating means are a microprocessor.

30. Apparatus as in claim 28 wherein a bi-directional counter is gated to the oscillator and the counter counts in an increasing direction pulses at the first frequency for a predetermined time, counts in a decreasing direction pulses at the second frequency for a time period equal to the predetermined time, and produces a residual count equal to the third value.

* * * * *

UNITED STATES PATENT AND TRADEMARK OFFICE
CERTIFICATE OF CORRECTION

PATENT NO. : 4,555,661

DATED : November 26, 1985

INVENTOR(S) : Benson et al.

It is certified that error appears in the above-identified patent and that said Letters Patent are hereby corrected as shown below:

Column 9, line 68, "electrode" should read --electrodes--;

Column 11, line 5, "freerunning" should read

--free-running--.

Signed and Sealed this

Eighteenth Day of March 1986

[SEAL]

Attest:

DONALD J. QUIGG

Attesting Officer

Commissioner of Patents and Trademarks